(12) United States Patent
Mazeris

(10) Patent No.: US 9,091,644 B2
(45) Date of Patent: Jul. 28, 2015

(54) ARRANGEMENT AND METHOD FOR FEEDING ANIMALS

(75) Inventor: Fernando Mazeris, Stockholm (SE)

(73) Assignee: DEVALAL HOLDING AB, Tumba (SE)

( * ) Notice: Subject to any disclaimer, the term of this patent is extended or adjusted under 35 U.S.C. 154(b) by 1814 days.

(21) Appl. No.: 10/581,924

(22) PCT Filed: Jan. 13, 2005

(86) PCT No.: PCT/SE2005/000024
§ 371 (c)(1),
(2), (4) Date: Jun. 7, 2006

(87) PCT Pub. No.: WO2005/067704
PCT Pub. Date: Jul. 28, 2005

(65) Prior Publication Data
US 2007/0134369 A1 Jun. 14, 2007

(30) Foreign Application Priority Data
Jan. 13, 2004 (SE) ...................................... 0400047

(51) Int. Cl.
*A01K 5/02* (2006.01)
*G01N 21/359* (2014.01)
*A01K 11/00* (2006.01)
*G01N 21/3563* (2014.01)

(52) U.S. Cl.
CPC ............... *G01N 21/359* (2013.01); *A01K 5/02* (2013.01); *A01K 5/0275* (2013.01); *A01K 11/006* (2013.01); *G01N 21/3563* (2013.01)

(58) Field of Classification Search
USPC ....................................................... 119/51.02
See application file for complete search history.

(56) References Cited

U.S. PATENT DOCUMENTS

| | | | | |
|---|---|---|---|---|
| 4,517,923 A | * | 5/1985 | Palmer | 119/51.02 |
| 4,712,511 A | | 12/1987 | Zamzow et al. | |
| 5,173,430 A | | 12/1992 | Edwards et al. | |
| 5,355,833 A | * | 10/1994 | Legrain | 119/51.02 |

(Continued)

FOREIGN PATENT DOCUMENTS

| | | |
|---|---|---|
| DE | 19940084 A1 | 3/2001 |
| EP | 0 974 264 A1 | 1/2000 |

(Continued)

OTHER PUBLICATIONS

Pierre Dardene et al., "Standardisation of Near Infrared Instruments, Influence of the Calibration Methods and the Size of the Cloning Set" Near Infrare Spectroscopy: Preceeding of the 10$^{th}$ International Conference, p. 23-28.

(Continued)

*Primary Examiner* — Son T Nguyen
(74) *Attorney, Agent, or Firm* — Young & Thompson

(57) ABSTRACT

An arrangement (12; 16) for feeding animals on a farm comprises an on-farm analyzer device (13; 17) provided for measuring, e.g. at least on a daily basis, the amount of a constituent of solid feed to be fed to said animals, and a feeding device (14; 18) provided for feeding said animals, wherein the feeding depends on the result of said measurement, and the amount of the constituent of solid feed is measured immediately prior to the feeding of said animals. By the arrangement, a proper solid feed mix with a balanced composition can be given to the animals.

50 Claims, 1 Drawing Sheet

(56) References Cited

U.S. PATENT DOCUMENTS

| | | | |
|---|---|---|---|
| 5,816,191 A | 10/1998 | Beaudoin et al. | |
| 5,878,402 A * | 3/1999 | Brewster et al. | 705/29 |
| 6,008,053 A | 12/1999 | Williams | |
| 6,076,043 A | 6/2000 | Liu | |
| 6,234,111 B1 * | 5/2001 | Ulman et al. | 119/54 |
| 6,532,420 B1 | 3/2003 | Haeffner et al. | |
| 6,556,948 B1 | 4/2003 | McKenna | |
| 6,681,717 B2 | 1/2004 | Burghardi et al. | |
| 6,837,189 B2 * | 1/2005 | Schick | 119/840 |
| 6,901,369 B2 * | 5/2005 | Cureton et al. | 705/1.1 |
| 7,308,866 B2 * | 12/2007 | Birk | 119/14.03 |
| 2002/0045265 A1 | 4/2002 | Bergh et al. | |
| 2002/0090442 A1 | 7/2002 | Haeffner et al. | |
| 2002/0120402 A1 | 8/2002 | Burghardi et al. | |
| 2003/0188689 A1 * | 10/2003 | Pratt | 119/51.02 |
| 2003/0226522 A1 * | 12/2003 | Thibault | 119/842 |
| 2003/0230245 A1 * | 12/2003 | Cheung | 119/174 |
| 2005/0000457 A1 * | 1/2005 | Beck | 119/51.02 |
| 2006/0041413 A1 * | 2/2006 | Burghardi et al. | 703/11 |

FOREIGN PATENT DOCUMENTS

| | | |
|---|---|---|
| EP | 1053671 A1 | 11/2000 |
| EP | 1 188 382 A1 | 3/2002 |
| EP | 1188382 A1 | 3/2002 |
| WO | WO 83/02158 | 3/1983 |
| WO | WO 8302158 A1 | 6/1983 |
| WO | 8911090 A1 | 11/1989 |
| WO | WO 92/03920 | 3/1992 |
| WO | WO 00/38501 | 7/2000 |
| WO | WO 01/14857 A1 | 3/2001 |
| WO | WO 01/29557 A2 | 4/2001 |
| WO | WO 01/69403 A1 | 9/2001 |
| WO | WO 2004/001651 A2 | 12/2003 |
| WO | WO 2005/067704 A1 | 7/2005 |

OTHER PUBLICATIONS

Paolo Berzaghi et al., "Comparison of Linear and Non-Linear Near Infrared Calibration Methods Using Large Forage Databases" Comparison of NIR Calibration Methods, p. 107-111.

Randy Shaver et al., "Feeding Systems and Strategies for Expanding Dairies" 4-State Expansion Conference, Mar.-Apr. 1998.

Pierre Dardene et al., "Standardisation of Near Infrared Instruments, Influence of the Calibration Methods and the Size of the Cloning Set" Near Infrare Spectroscopy: Proceeding of the $10^{th}$ International Nir Conference in Hyongju, South Korea, pp. 23-28 (Jun. 11-15, 2001).

Paolo Berzaghi et al., "Comparison of Linear and Non-Linear Near Infrared Calibration Methods Using Large Forage Databases" Comparison of NIR Calibration Methods; Proceeding of the $10^{th}$ International NIR Conference in Hyongju, South Korea, pp. 107-111 (Jun. 11-15, 2001).

"Herd Health and Production Management in Dairy Practice" by A. Brand, J.P.T.M. Noordhuizen, Y.H. Schukken, published by Wageningen Academic Publishers in 1996, ISBN: 978-90-74134-34-7 and English translation.

"Lantbrukets husdjur", Third Revised Edition, third printing, 1992, ISBN 91-36-02505-4.

Notice of Opposition dated Dec. 3, 2014, filed in the corresponding EP application 07019590.4.

Notice of Opposition dated Dec. 4, 2014, filed in the corresponding EP application 07019590.4.

\* cited by examiner

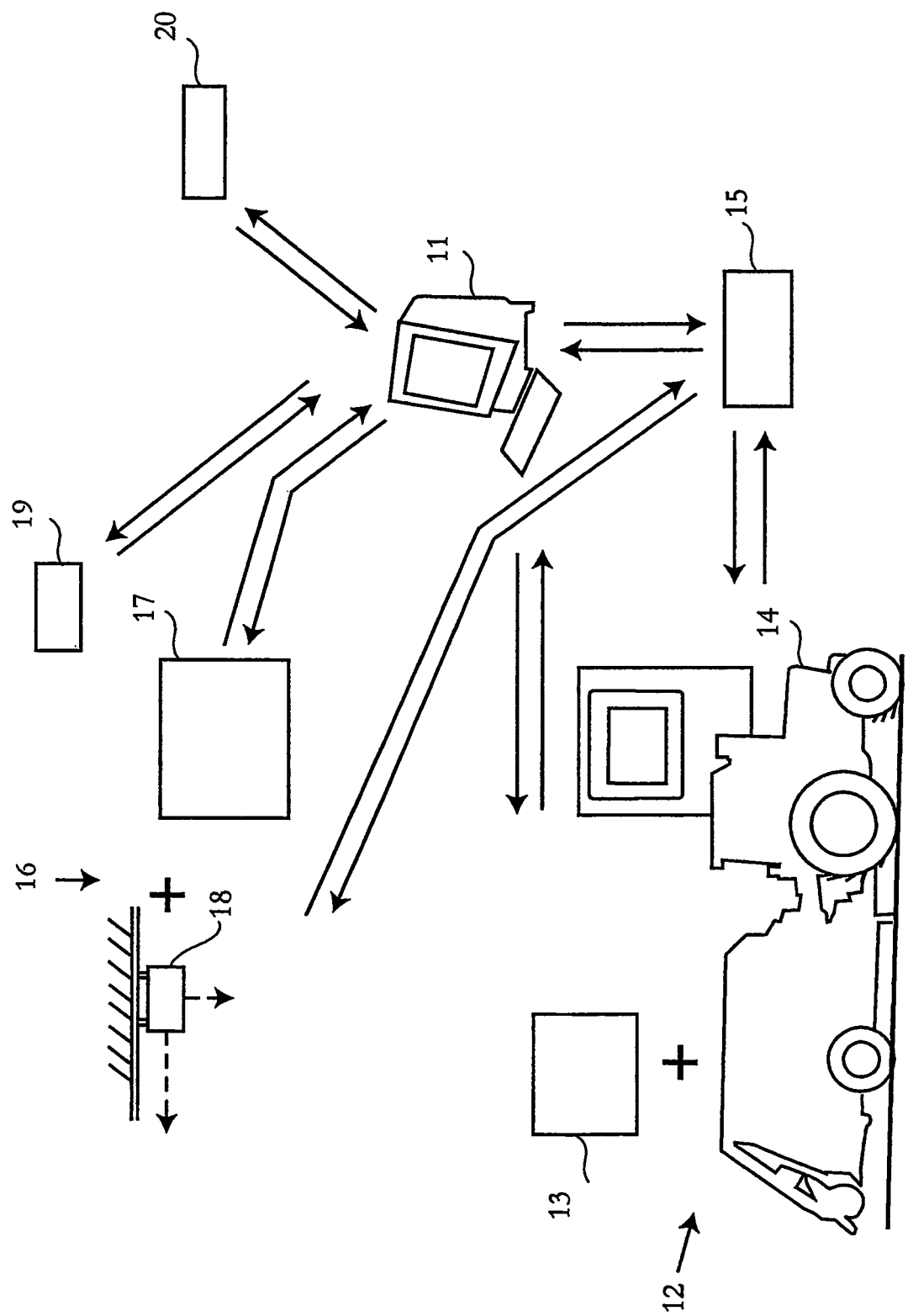

ARRANGEMENT AND METHOD FOR FEEDING ANIMALS

TECHNICAL FIELD OF THE INVENTION

The present invention generally relates to farming, and more specifically the invention relates to an arrangement and a method for feeding animals.

DESCRIPTION OF RELATED ART AND BACKGROUND OF THE INVENTION

Feed costs comprise 40-50% of the cost of milk production. Implementation and management of feeding systems to sustain high levels of milk production and control feed costs are crucial to the profitability of expanding dairies. Considerations regarding nutritional demands of the herd (including grouping), ration management (includes analysis of the feed, cost and availability), feeds preparation and transport, feed distribution and consumption control have to be made.

In the US total mixed ration (TMR) is the predominant method of feed delivery on larger farms. The cows are grouped according to their level of milk production and body condition. Each group is then fed with total mixed ration feed independently to reduce over-feeding of nutrients and therefore feed costs. In Europe, on the other hand, the farms are smaller, and typically, the animals have unlimited supply of roughage, whereas concentrate and optionally minerals, vitamins, and trace elements are given individually to each animal.

The quality of anaerobically fermented or ensiled feed is dependent on the quality of the crude feed, the conditions of ensiling, and the conditions of storage of the ensiled feed. For instance, aerobic deterioration of ensiled feeds is detrimental to the milk production. Aerobic microorganisms such as yeasts, molds and certain bacteria metabolize the highly-digestible fraction of the dry matter and can account for high losses of dry matter.

Attempts have been made to increase the efficiency of feed utilization and milk production by using various formulations and feed supplements. Despite continued improvement in the development of dairy cattle feed rations, it is desirable to further increase the efficiency of feed utilization and milk production by dairy cattle.

SUMMARY OF THE INVENTION

In order to obtain information of the composition of the ensiled feed, samples may be taken and sent to a laboratory for analyze, and the amounts of various constituents may be derived. By such knowledge a more precise feeding can be performed. However, to obtain a more optimum feeding of animals in terms of feed composition, feed costs and milk production, such a method may not be sufficient. It may for instance be too long delays between the preparation of the sample and when analyze results are received, and samples may be taken too rarely. For instance, the composition of the feed, especially ensiled feed, may vary over time, and as a result the animals may be over- or underfed with some constituents of the feed.

It is therefore an object of the present invention to provide an arrangement and a method for feeding animals on a farm, which are more precise, and which can reduce the feeding costs and increase the quantity and/or quality in milk production.

It is a further object of the invention to provide such an arrangement and method, which can be fully automated, and which can be coupled to a computer-based managing and control device for overall management of the animals on the farm.

It is still a further object to provide such an arrangement and method, which are uncomplicated, reliable, of low cost, and easy to implement.

These objects, among others, are according to the present invention attained by arrangements and methods as specified in the appended claims.

It has been established that that the composition of feed, particularly but not solely ensiled feed, varies quite much from day to day, and even from time to time during the day, and that these variations naturally affect the amounts or balance of various nutrients given to the animals in an adverse manner when feeding with fixed rations, and consequently also the milk production is deteriorated.

Further, the composition of feed may vary from spot to spot within a feed storage arrangement such as a fodder silo depending on parameters such as temperature, humidity, and oxygen supply of the immediate environment of the feed at the particular spot. That is, different portions of the feed may have different compositions.

By the provision of an on-farm analyzer device, which measures at least on a daily basis the amount of a constituent of solid feed to be fed to the animals, and a feeding device, which feeds the animals depending on the measured amount of the constituent of the solid feed, a more precise feeding can be effectuated. Preferably, feed is analyzed at different locations in the feed storage arrangement that stores the feed.

Preferably, the amounts of several constituents, such as e.g. protein content, dry content, and fiber content, particularly neutral detergent fiber (NDF) of the solid feed, are monitored. Measurements may be effectuated immediately prior to each feeding of the animals.

The on-farm analyzer device, which may be a spectroscopic device for quantitative chemical analysis such as e.g. a near infrared (NIR) instrument, measures advantageously the amount of the constituent of the solid feed immediately prior to each feeding of the animals to obtain a real time measurement of the instantaneous composition of the solid feed. It is noticed that the instrument may be located anywhere on the farm, and it may be arranged for manual as well as for automatic measurement.

The amount of suitable feed may be calculated to achieve maximum profit, maximum milk production, or milk of a desired quality. The feeding arrangement is adapted to be implemented in a total mixed ration (TMR) feeding program with group-wise feeding of the animals, or in an arrangement wherein the animals have supply of partial mixed rations (PMR) of feed, including ensilage and concentrate, and wherein the animals are fed with additional concentrate feed individually and depending on the measured amount of the constituent of the solid feed. Alternatively, the animals are grouped in different groups e.g. according their milk production (if the animals are milk producing animals) and body condition, and wherein different groups of animals are fed with roughage or ensiled feed independently, and optionally depending on the measured amount of the constituent of the solid feed, and the animals are fed with concentrate feed on an individual basis and depending on the measured amount of the constituent of the solid feed.

Thus, the present invention may be utilized for feeding of a complete herd of animals, for feeding different groups of animals differently, as well as for feeding each single animal of the herd independently depending on the measured amount of the constituent of the solid feed.

In one advantageous embodiment a computer-based processing and control device is provided for the management of the animals including controlling of the feeding of the animals, and comprises a database including updated information regarding feed consumption by the animals. The processing and control device is connected to receive the respective measured amounts of the constituent of the solid feed from the on-farm analyzer device, and calculates a suitable amount of solid feed of a suitable composition to be fed to the animals based on the measured amount of the constituent of the solid feed and the updated information comprised in the database. Finally, the processing and control device indicates to the feeding device the calculated amount of suitable feed to be fed to the animals. The feeding arrangement may in this manner be fully automatic.

In order to determine the actual feed consumption by the animals, individually, group-wise or totally by the complete herd, a device, preferably a weighing machine or an optical device with image processing capabilities is provided for measuring in connection with each of the feedings, the actual amount of feed consumed by the animals. The feeding of the animals may then be modified according to their previous actual feed consumption.

Further, devices, methods and/or means may be provided for (i) analyzing the milk from the animals provided that the animals are milking animals, e.g. for determining content of fat, protein, lactose, solids-not-fat and somatic cells, urea, or BHB, (ii) analyzing the manure from the animals, and (iii) analyzing the body condition of the animals, e.g. for determining the weight and health of the animals. The animals can then be fed depending on some or all of the above data on an animal individual, or group-wise basis.

In addition, according to a further aspect of the present invention an analyzer device is provided on a farm housing animals. The analyzer device is provided to measure the amount of a constituent of solid feed to be fed to the animals on the farm; and includes means provided to transfer the measured amount of the constituent of the solid feed to a feeding device provided for feeding the animals depending on the measured amount of the constituent of the solid feed.

Further characteristics of the invention and advantages thereof, will be evident from the following detailed description of preferred embodiments of the present invention given hereinafter and the accompanying FIG. 1, which is given by way of illustration only and thus, is not limitative of the present invention.

BRIEF DESCRIPTION OF THE DRAWINGS

FIG. 1 displays schematically a preferred embodiment of a feeding system according to the present invention.

DETAILED DESCRIPTION OF PREFERRED EMBODIMENTS

In the following detailed description the animals are cows. However, the invention is not limited to cows, but is applicable to any animals having the capability to produce large quantities of milk, such as sheep, goats, horses, etc., as well as to beef cattle, and the like. In the latter instance, the descriptions below regarding milk production, milk control, milk analyze etc. can be disregarded.

A preferred embodiment of a complete system for feeding cows on a dairy farm according to the present invention is schematically illustrated in FIG. 1.

A computerized cow managing device 11 is provided for the management and control of the cows on the dairy farm.

The cow managing system 11 may control and monitor milking, feeding, milk inspection, milk sampling, cow traffic, etc. in an area wherein the cows are walking about freely. To this end, the cow managing system 11 typically comprises a microcomputer, suitable software, and a database including information of each of the cows on the dairy farm, such as e.g. when the respective cow was milked last time, when she was fed last time, how much she was fed last time, her milk production, her health, etc.

A first inventive arrangement for feeding the cows on the dairy farm is indicated by reference numeral 12 and comprises an on-farm analyzer device 13 and a feeding vehicle 14.

The on-farm analyzer device 13 is provided for analyzing at least on a daily basis, the composition of solid feed to be fed to the cows and for determining the amount of one or several constituents of the solid feed. The solid feed may include roughage, grass, grain and corn, or any kind of ensiled feed, and the one or several constituents, of which the amount is determined, may include any of protein, dry matter, and fiber, particularly neutral detergent fiber (NDF). Other constituents of the solid feed that can be measure include moisture, fat, starch, TKN, crude fiber, acid detergent fiber (ADF), and lignin according to relevant ISO, EC and AOAC standards. Still other constituents of solid feed to be measured include vitamins and minerals.

The on-farm analyzer device 13 may measure the amount of the solid feed constituent several times per day if appropriate, e.g. immediately prior to each of the feeding instants.

Alternatively or additionally, the on-farm analyzer device 13 may analyze feed stored at different locations in a silo, or in different feed supply or storage devices.

The on-farm analyzer device 13 is preferably a spectroscopic device for quantitative chemical analysis, and more preferably a near infrared (NIR) instrument based on e.g. a near infrared reflectance spectroscopy technique. Documents describing near infrared (NIR) instruments for use in the present invention include the International Patent publication No. WO 01/14857 A1, *Near Infrared spectroscopy*, Edited by R. K. Cho and A. M. C. Davies, Proceedings of the $10^{th}$ International Conference, NIR Publications, pp 23-28, 2001; and *Comparison of linear and non-linear near infrared calibration methods using large forage databases*, P. Berzaghi et al., pp 107-111, as well as references mentioned therein, the contents of which being hereby incorporated by reference.

The latter article describes comparison of various calibration methods using large forage databases. The amount of forage data growths fastly and will provide for the development of better global calibration methods in order to obtain more accurate absolute values of the amounts of different constituents of the solid feed.

The on-farm analyzer device 13 can be an apparatus existing commercially today, but preferably a simplified, faster and cheaper apparatus designed for the field should be used. By means of having the analyzer device 13 on the farm for in-situ measurements, real time or near real time values of the composition of the solid feed can be provided.

The on-farm analyzer device 13 may comprise different apparatuses for measurements of different constituents. Preferably, the on-farm analyzer device measures the composition of all feed ingredients to provide for a more accurate ration balancing so that the cows can maximize their production.

The feeding vehicle 14 of the feeding arrangement 12 is provided for feeding the cows, at each instant, depending on the measured amount of the one or several constituents of the solid feed. The feeding vehicle may be a truck or trailer filled with the solid feed, and the on-farm analyzer device 13 is advantageously mounted at the truck or trailer for measuring the amount of the solid feed constituent.

A feed management module 15 is provided as a separate module in the computerized cow managing device 11, as a stand-alone device, or as being incorporated in the arrangement 12. The feed management module 15, which in any case is connected to communicate with the cow-managing device 11 and the arrangement 12, fetches updated information regarding milk production and feed consumption by the cows and the respective measured amounts of the solid feed constituent. The feed management module 15 calculates repeatedly (prior to each feeding instant) an amount of feed to be fed to the cows based on, at each instant, the measured amount of the solid feed constituent and the updated information, and indicates, preferably to the arrangement 12 or the feeding vehicle 14, the calculated amount of feed to be fed to the cows at each instant.

By means of the inventive arrangement 12, more precise feeding can be effectuated. An exact amount of feed ingredients and nutrients can be given to each cow, while the feed costs are kept at a minimum and the milk production is kept at a maximum.

It shall be noted that the feeding vehicle 14 may be provided for feeding the cows with mixed feed with a balanced composition, at each instant, depending on the measured amount of the solid feed constituent, or that the feeding vehicle 14 is provided for feeding the cows with roughage, ensilage, concentrate feed or other feed additive such as e.g. minerals and vitamins, at each instant, depending on the measured amount of the solid feed constituent. In the former instance, the feed mix is given in accurate amounts at each instant to compensate for any variations as measured so that the cow will receive the necessary nutrients. In the latter instance, some feed ingredient may be given in suitable amounts, at each instant, to compensate for any variations in the composition of the solid feed mix.

The system of FIG. 1 comprises also a second inventive feeding arrangement 16. The second arrangement 16 comprises an on-farm analyzer device 17 and a feeding device 18. The on-farm analyzer device 17 may be identical with or similar to the on-farm analyzer device 13 of the first feeding arrangement 12. However, the feeding device 18 is provided as a feed wagon, preferably an in-door feed wagon mounted on a rail in a ceiling, for automatic feeding of the cows. The second arrangement 16 is also connected to the feed management module 15 and to the computerized cow managing device 11, and operates similar to the arrangement 12. However, here a fully automated management and feeding system is provided which may handle ration calculation and feeding completely automatically.

The arrows in FIG. 1 indicate communication links between the different parts of the inventive system for feeding cows. Provided that each component is provided with a microcomputer and transceiver (or directly connected cable) the communication as well as the operation of the system can be fully automated.

It shall be appreciated by the man skilled in the art that the present invention may comprise only one of the feeding arrangements 12, 16. Likewise, the two feeding devices, the feeding vehicle 14 and the feed wagon 18, may be connected to a single on-farm analyzer device and to obtain the measured amounts of solid feed constituents from this single on-farm analyzer device.

The present invention is suitable for use in combination with TMR (total mixed ration) feeding programs, PMR (partially mixed ration programs), or other modified feeding programs.

TMR, or complete rations, are defined as those with all the roughage, ensilage, concentrate and grain ingredients blended together, formulated to specific nutrient concentration, and fed free choice. TMR has become very attractive in the US for large dairy farms, e.g. those housing several hundred and up to several thousand cows. The main advantages of TMR feeding are that cows consume the desired proportion of feed when two or more feed ingredients are offered; feed efficiency improves; it allows for greater use of unpalatable feeds, NPN sources, and commodity feeds; and it allows for greater accuracy in formulating and feeding. The potential disadvantages include that TMR requires a significant equipment investment in a mixer; the cows have to be grouped into two or more groups; rations must be carefully formulated and continually checked; and pasture feeding and large amounts of long hay are difficult to incorporate into rations.

Dividing cows into production strings is a critical factor for the success of TMR feeding. The cows are typically grouped in different groups according their milk production and body condition. For instance, the cows may be grouped into the following groups: fresh cows, high producing older cows, high production first calf heifers, and cows with low or excess body condition. In larger herds more groups can be defined to obtain about 100 cows in each group.

The feeding arrangement 12 (and/or 16) of the present invention can be used for feeding different groups of cows with total mixed rations of feed, including the analyzed feed, independently, and, at each instant, depending on the measured amount of the solid feed constituent. The ration formulation (i.e. the relative amount of the various ingredients in the total mixed ration) as well as the total amount of feed to be given to the cows can be determined based on result of the on-farm analyzer device 13 (and/or 17) of the present invention.

PMR is used frequently throughout Europe, particularly at smaller dairy farms, and in this program at least one component of the feed is given to the cows on an individual basis. Typically, the cows may have unlimited supply of roughage, whereas concentrate feed and/or feed additives (including grains, minerals and vitamins) are given to the cows individually. The advantage is that high cost feed ingredients (e.g., protected fats, high bypass protein supplements, special mineral packs) can be specifically targeted to individual cows. The disadvantage of additional grain feeding is excessive amounts can unbalance the feeding balance reducing fiber and forage intakes.

While using the present invention in the above-identified PMR program, the feed device 18 is provided for feeding each of the cows with concentrate feed individually, and, at each instant, depending on the measured amount of the solid feed constituent. E.g., if it is noted that the cows obtain too small quantities of a particular nutrient from the feed due to low contents of it in silage, higher quantities of the nutrient may be added to the concentrate. Also, since the concentrate is given to the cows individually, the concentrate can be given in different amounts to different individuals.

In a modified PMR version, the cows are grouped in different groups e.g. according their milk production and body condition, and cows of different groups are given different partially mixed rations of feed including ensilage, whereas the concentrate feed and/or feed additives are given to the cows, as above, individually. Here the feed device 18 of the present invention is provided for (i) feeding different groups of cows with the PMR feed (including ensilage) independently, and at each instant, depending on the measured amount of the solid feed constituent, and (ii) feeding the cows with concentrate feed or feed additives on an individual basis, and, at each instant, depending on the measured amount of the solid feed constituent.

In another feeding program each cow is given in principle all its feed (solid and optionally liquid) on an individual basis. Automatic feeding stations known in the art may be used to give each cow, after the cow has been identified by an automatic identifying device, precise and accurate feed rations at each instant, where these precise and accurate feed rations are determined at each instant depending on the measured amount of the solid feed constituent.

It shall be noted that the feeding arrangements 12, 16 of the present invention may also comprise apparatuses (the devices 13, 17 or others) capable of analyzing mixed feed and determine various constituents or ingredients in the mix, wherein the feeding arrangements 12, 16 may base their feeding on the result of such analysis.

Measurements may be performed on samples of the individual ingredients of a food mixture before the different ingredients are mixed together, wherein the mixing is performed based on the result of the measurements of the samples. Certain parameters, such as the humidity value, of the different ingredients will directly affect the amount of a specific ingredient in the food mix, whereas other parameters, such as protein, has to deviate to a certain degree from an acceptable level before the amount of the ingredient in question in the mix is changed. The percentage of the different ingredients in a mixture shall, however, not be changed to often since problems may arise such as the digestion of the animals.

It shall be appreciated by the man skilled in the art that the feeding may be performed based on the last measured amount of feed constituent, or on some average of a number of measurements performed.

In order to obtain even more precise and accurate feeding of the cows, further information of the feed given to the cows and of the cows themselves are required. In order to fulfill such requirements, the present invention features a device 19, preferably a weighing machine or an optical device with image processing capabilities, provided for measuring in connection with each of the feedings, the actual feed consumption by the cows. This may be performed on a cow individual basis, for groups of cows, or commonly for a complete herd. The feeding of the cows, individually, group-wise or commonly for the herd, can then, at each instant, be dependent on measured actual feed consumption by the cows.

Further, a device 20, schematically indicated in FIG. 1, is provided for analyzing milk from the cows, for analyzing the condition of the cows, and/or for analyzing manure from the cows. Milk analyzer apparatuses are known in the art. In connection with the milking of the cows, the milk is measured and analyzed to reveal e.g. protein and fat contents, the conductivity, the somatic cell count etc. Some of these milk quality parameters are related to the health of the cows. Other apparatuses for measuring the condition of the cows include activity meters, weighing devices, and inspection devices. Evaluation of manure can provide information on rumen function and digestion of the feed ration. Milk, cow health and manure evaluation can thus help to diagnose areas for improvement in both ration formulation and feed management. Therefore, the feeding of the cows, individually, group-wise or commonly for the herd, can, at each instant, be dependent on the data related to the milk produced by the cows, to the condition or health of the cows, and to the manure of the cows.

The invention claimed is:

1. A feeding system for feeding animals on a farm, comprising:
    an analyzer device for measuring in real time or near real time an amount of at least one constituent of solid feed to be fed to said animals;
    a feeding device for feeding said animals; and
    a control device,
    wherein the control device is configured to control the analyzer device to repeatedly measure the amount of the constituent of the solid feed at least once a day,
    wherein the amount of said constituent includes any one of a protein content, a fiber content, and a neutral detergent fiber (NDF) content, and
    configured to control the feeding device to feed said animals repeatedly and at each instance based on the previous said repeatedly performed measurements;
    wherein the analyzer device further samples individual ingredients of a food mixture which make up the solid feed, wherein the sampling of the individual ingredients of the food mixture is performed before the individual ingredients are mixed together, wherein the mixing is performed based on a result of a measurement of the samples.

2. The system of claim 1, wherein the control device is configured to control said analyzer device to measure the amount of said constituent of said solid feed immediately prior to the feeding of said animals.

3. The system of claim 2, wherein the analyzer device measures the amount of at least one constituent of solid feed to be feed to said animals at different locations in a feed supply device.

4. The system of claim 3, wherein said feeding device is a vehicle filled with said solid feed, and said analyzer device is provided at said vehicle for measuring the amount of said constituent of said solid feed.

5. The system of claim 2, wherein said feeding device is a vehicle filled with said solid feed, and said analyzer device is provided at said vehicle for measuring the amount of said constituent of said solid feed.

6. The system of claim 5, wherein said vehicle is an in-door feed wagon mounted on a rail in a ceiling, for automatic feeding.

7. The feeding system of claim 2, wherein the amount of the at least one constituent of the solid feed is measured and the animals are fed in real time in situ.

8. The system of claim 1, wherein the control device is configured to control said analyzer device to measure the amount of said constituent of said solid feed a plurality of times per day.

9. The system of claim 1, wherein said solid feed is ensiled feed.

10. The system of claim 1, wherein the control device is configured to control said analyzer device to measure the amounts of a plurality of constituents of said solid feed, and configured to control said feeding device to feed said animals depending on the measurements of the amounts of the constituents of said solid feed.

11. The system of claim 1, wherein the control device is configured to control said feeding device to perform said feeding depending on an average value of said repeatedly measured amounts of said constituent.

12. The system of claim 1, wherein said analyzer device is a spectroscopic device for quantitative chemical analysis.

13. The system of claim 1, wherein said analyzer device is a near infrared (NIR) instrument.

14. The system of claim 1, wherein the control device is a computer-based processing and control device provided for managing of said animals including controlling of the feeding of said animals, wherein said computer-based processing and control device includes:
a database including updated information regarding feed consumption by said animals;
is connected to receive said respective measured amounts of said constituent of said solid feed;
is provided to calculate an amount of solid feed to be fed to said animals based on the performed measurements and said updated information included in said database; and
is connected to indicate to said feeding device said calculated amount of solid feed to be fed to said animals.

15. The system of claim 1, wherein the control device is configured to control said feeding device to feed said animals with mixed solid feed having a balanced composition depending on the performed measurements.

16. The system of claim 1, wherein the control device is configured to control said feeding device to feed said animals with solid feed having ensilage and concentrate and/or additives depending on the performed measurements.

17. The system of claim 1, wherein said animals are grouped in different groups, such that the control device is configured to control said feed device to feed different groups of animals with total mixed rations (TMR) of solid feed independently and in accordance with the performed measurements.

18. The system of claim 17, wherein said animals are grouped in different groups depending on body condition and, provided that the animals are milking animals, depending on milk production, days in lactation, or number of lactations.

19. The system of claim 1, wherein said animals have a supply of partial mixed rations (PMR) of solid feed, including ensilage and concentrate, such that the control device is configured to control said feed device to feed each of said animals with additional concentrate feed individually and in accordance on the performed measurements.

20. The system of claim 1, wherein said animals are grouped in different groups, such that the control device is configured to control said feed device to (i) feed different groups of animals with roughage or ensilage depending on the performed measurements, and (ii) feed said animals with concentrate or additives individually and in accordance on the performed measurements.

21. The system of claim 1, wherein the control device is configured to control said feed device to feed different individuals of said animals with solid feed individually depending on the performed measurements.

22. The system of claim 1, wherein said feeding device is a vehicle filled with said solid feed, and said analyzer device is provided at said vehicle for measuring the amount of said constituent of said solid feed.

23. The system of claim 1, wherein said feeding device is an in-door feed wagon mounted on a rail in a ceiling, for automatic feeding.

24. The system of claim 1, further comprising a weighing machine or an optical device with image processing capabilities, provided for establishing in connection with said feeding, the actual feed consumption by said animals, wherein the control device is configured to control said feeding device to feed said animals depending on the established actual feed consumption by said animals.

25. The system of claim 1, wherein said animals are milking animals, further comprising a device provided for measuring a quality or a quantity of milk from said milking animals, and the control device is configured to control said feeding device to feed said milking animals depending on the measured quality or quantity of milk from said milking animals.

26. The system of claim 1, further comprising a device for measuring a quality of manure from said animals, wherein the control device is configured to control said feeding device to feed said animals depending on the measured quality of manure from said animals.

27. The system of claim 1, wherein the control device is configured to control said analyzer device to measure the amount of the constituent of the solid feed repeatedly and at least once a day automatically.

28. The system of claim 1, wherein the control device is configured to control said feeding device to feed said animals repeatedly and at each instance depending on the last one of said repeatedly performed measurements automatically.

29. The system of claim 1, wherein the control device comprises:
an analyzer control device to control the analyzer device to measure the amount of the constituent of the solid feed repeatedly and at least once a day; and
a feed control device for controlling the feed device to feed said animals repeatedly and at each instance based on the previous said repeatedly performed measurements.

30. The system of claim 1, wherein the control device is configured to control said analyzer device to measure the amount of said constituent of said solid feed at least three times per day.

31. The system of claim 1, wherein the analyzer device measures the amount of at least one constituent of solid feed to be feed to said animals at different locations in a feed supply device.

32. The system of claim 1, wherein the analyzer device measures all of the constituents of the solid feed to provide more accurate ration balancing and maximized production.

33. The system of claim 1, wherein the analyzer device is a spectroscopic device which measures quantitative chemical analysis.

34. The system of claim 33, wherein the spectroscopic device is a near infrared (NIR) instrument based on near infrared reflectance spectroscopy technique.

35. The system of claim 1, wherein the analyzer device measures the amount of the at least one constituent of the solid feed to be fed to said animals at different locations within a storage device.

36. The system of claim 1, further comprising an optical device with image processing capabilities for measuring the actual feed consumption in connection with each of the feedings.

37. The system of claim 1, wherein different groups of animals are fed with total mixed rations of feed, independently, and at each instance, depending on the measured amount of the at least one constituent of solid feed.

38. The system of claim 1, wherein the measured constituent include any one of vitamins, minerals, moisture, fat, starch, TKN, crude fiber, acid detergent fiber (ADF), and lignin.

39. The feeding system of claim 1, wherein at least the animals, the analyzer device, and the feeding device are colocated.

40. The feeding system of claim 1, wherein at least the animals, the analyzer device, and the feeding device are in situ.

41. Use of a feeding system comprising an analyzer device and a feeding device for feeding animals, said analyzer device, performed by a control device, for measuring in real time or near real time, repeatedly, and at least once a day the amount of at least one constituent of solid feed to be fed to said animals, and said feeding device, performed by the control device, being used for feeding said animals repeatedly and at each instance based on the previous said repeatedly performed measurements, wherein the amount of said constituent includes any one of a protein content, a fiber content, and a neutral detergent fiber (NDF) content; wherein the analyzer device further samples individual ingredients of a food mixture which make up the solid feed, wherein the sampling of the individual ingredients of the food mixture is performed before the individual ingredients are mixed together, wherein the mixing is performed based on a result of a measurement of the samples.

42. The use of claim 41, wherein the control device is configured to control said analyzer device to measure the amount of said constituent of said solid feed immediately prior to the feeding of said animals.

43. The use of claim 41, wherein the control device is configured to control said analyzer device to measure the amount of said constituent of said solid feed a plurality of times per day.

44. The use of claim 43, wherein the control device is configured to control said analyzer device to measure the amount of said constituent of said solid feed at least three times per day.

45. The use of claim 41, wherein the analyzer device measures the amount of at least one constituent of solid feed to be feed to said animals at different locations in a feed supply device.

46. The use of claim 41, wherein said feeding device is a vehicle filled with said solid feed, and said analyzer device is provided at said vehicle for measuring the amount of said constituent of said solid feed.

47. The use of claim 46, wherein said vehicle is an in-door feed wagon mounted on a rail in a ceiling, for automatic feeding.

48. The use of claim 41, wherein the analyzer device measures all of the constituents of the solid feed to provide more accurate ration balancing and maximized production.

49. The use of claim 41, wherein the analyzer device is a spectroscopic device which measures quantitative chemical analysis.

50. The use of claim 49, wherein the spectroscopic device is a near infrared (NIR) instrument based on near infrared reflectance spectroscopy technique.

* * * * *